(12) United States Patent
Keays

(10) Patent No.: US 8,381,573 B2
(45) Date of Patent: Feb. 26, 2013

(54) SOBRIETY MONITORING SYSTEM

(76) Inventor: Brad Keays, Manhattan Beach, CA (US)

( * ) Notice: Subject to any disclaimer, the term of this patent is extended or adjusted under 35 U.S.C. 154(b) by 295 days.

(21) Appl. No.: 12/882,323

(22) Filed: Sep. 15, 2010

(65) Prior Publication Data

US 2011/0079073 A1    Apr. 7, 2011

Related U.S. Application Data

(60) Provisional application No. 61/320,168, filed on Apr. 1, 2010, provisional application No. 61/254,575, filed on Oct. 23, 2009, provisional application No. 61/248,364, filed on Oct. 2, 2009.

(51) Int. Cl.
*G01N 33/497* (2006.01)

(52) U.S. Cl. .......................... 73/23.3; 422/84

(58) Field of Classification Search ................. 73/23.3; 422/84
See application file for complete search history.

(56) References Cited

U.S. PATENT DOCUMENTS

| | | | |
|---|---|---|---|
| 6,726,636 | B2 | 4/2004 | Der Ghazarian et al. |
| 6,748,792 | B1 * | 6/2004 | Freund et al. ................. 73/23.3 |
| 6,837,095 | B2 * | 1/2005 | Sunshine et al. .............. 73/23.2 |
| 6,899,683 | B2 * | 5/2005 | Mault et al. ................... 600/531 |
| 7,341,693 | B2 | 3/2008 | Der Ghazarian et al. |
| 7,462,149 | B2 | 12/2008 | Hawthorne et al. |
| 7,611,461 | B2 | 11/2009 | Hawthorne et al. |
| 7,636,047 | B1 | 12/2009 | Sempek |
| 7,641,611 | B2 | 1/2010 | Hawthorne et al. |
| 7,841,224 | B2 * | 11/2010 | Son ............................... 73/1.02 |
| 8,280,436 | B2 * | 10/2012 | Harris, Jr. ..................... 455/556.1 |
| 2002/0127145 | A1 | 9/2002 | Der Ghazarian et al. |
| 2004/0239510 | A1 * | 12/2004 | Karsten ......................... 340/576 |
| 2006/0202838 | A1 | 9/2006 | Hawthorne et al. |
| 2007/0239992 | A1 | 10/2007 | White et al. |
| 2008/0009693 | A1 | 1/2008 | Hawthorne et al. |
| 2008/0183502 | A1 | 7/2008 | Dicks et al. |
| 2008/0314115 | A1 * | 12/2008 | Faulder et al. ................. 73/23.3 |
| 2009/0053110 | A1 * | 2/2009 | Chang et al. ................... 422/84 |
| 2009/0182216 | A1 | 7/2009 | Roushey, III et al. |
| 2009/0201138 | A1 | 8/2009 | Ghazarian et al. |
| 2009/0293589 | A1 * | 12/2009 | Freund et al. .................. 73/23.3 |
| 2010/0089121 | A1 * | 4/2010 | Hemmingsson et al. ...... 73/23.3 |
| 2010/0138166 | A1 * | 6/2010 | Do et al. ........................ 702/24 |
| 2010/0251804 | A1 * | 10/2010 | Morley et al. ................. 73/23.3 |
| 2012/0031166 | A1 * | 2/2012 | Lopez et al. ................... 73/23.3 |

OTHER PUBLICATIONS

CNET Reviews, "iBreath: the iPhone Breathalyzer," <http://reviews.cnet.com>, published online on Dec. 15, 2008.*
Intoxalock Overview: Mobile eLERT Camera, <http://intoxalock.com/mobile-elert-camera.cfm>, print date: Dec. 4, 2012.*
Electronic Monitoring System, MEMS 3000 Homestation Installation Guide, ElmoTech Ltd., Mar. 2006.*
International Search Report, PCT/US2010/050930, Apr. 3, 2012.
http://www.web.archive.org/web/20090311081549/ http://alcoholmonitoring.com/index/scram/what-is-scram, Nov. 3, 2009.
http://www.intoxalock.com/intoxalock-alcohol-monnitoring-systems.cfm, print date: Oct. 15, 2012.

* cited by examiner

*Primary Examiner* — Lisa Caputo
*Assistant Examiner* — Punam Roy
(74) *Attorney, Agent, or Firm* — One LLP

(57) ABSTRACT

A system and method of monitoring sobriety using a handheld breath testing device that, on receipt of a user's breath, generates a breath test signal comprising substance content data and user identification data, and wirelessly transmits the breath test signal to a breath test signal receiving station. The breath test signal includes substance content data and user identification data. The substance content data includes a blood alcohol level and the user identification data includes compressed image data. The signal receiving station is monitored by a supervisor who is able to intervene should the blood alcohol level be greater than a predetermined threshold, or should the user identification data no match with a reference user identification data.

22 Claims, 7 Drawing Sheets

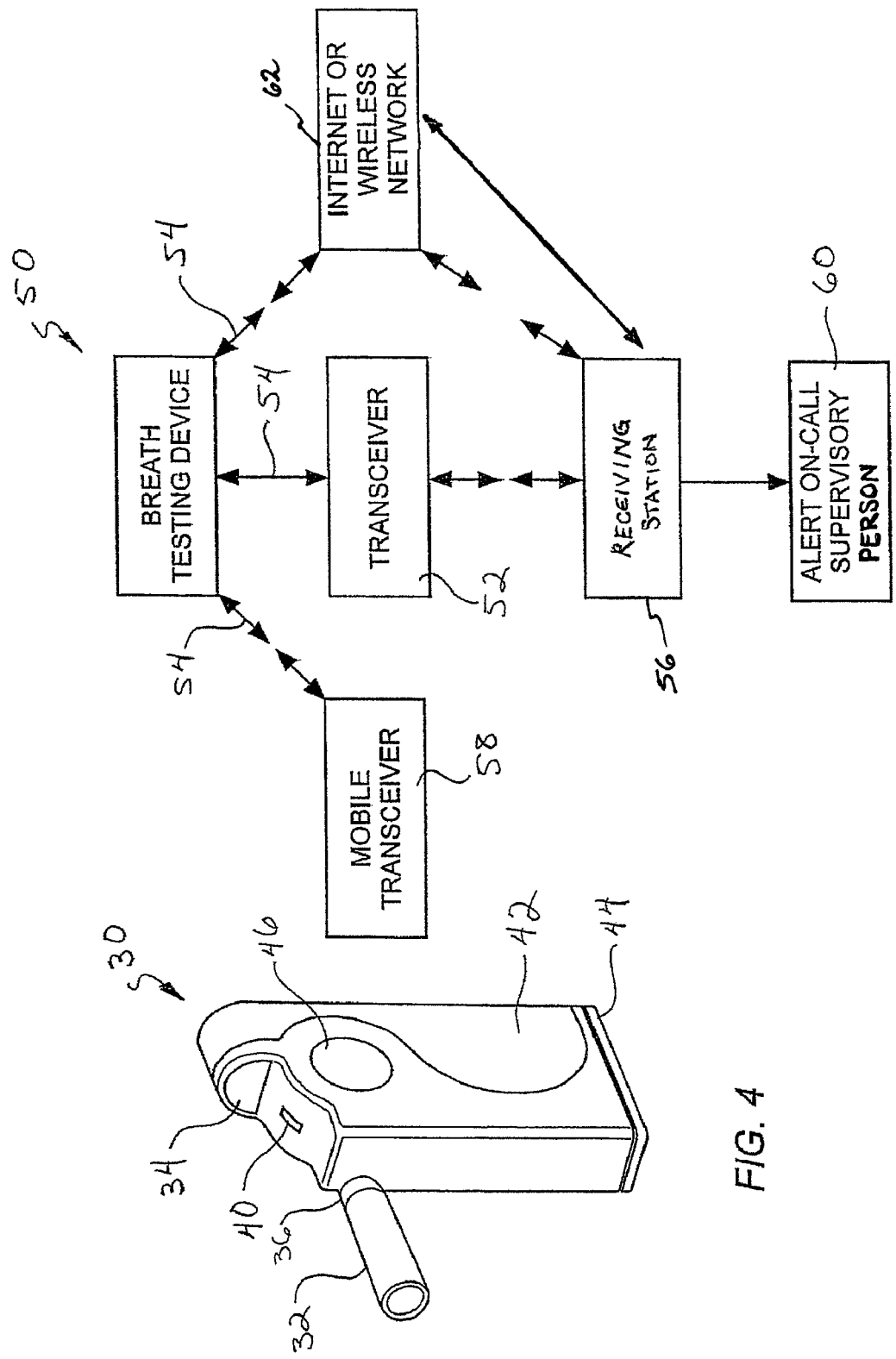

SOBRIETY MONITORING SYSTEM

CROSS-REFERENCE TO RELATED APPLICATIONS

Related to U.S. Provisional Application No. 61/320,168; filed Apr. 1, 2010; U.S. Provisional Application No. 61/254,575 filed Oct. 23, 2009; and U.S. Provisional Application No. 61/248,364, filed Oct. 2, 2009.

BACKGROUND OF THE INVENTION

Field of the Present Disclosure

This disclosure relates generally to a method and system for remote sobriety monitoring, and more particularly relates to a method and system utilizing a breath testing and identification device for periodically analyzing the alcohol content or other substance content of the breath of a user in combination with a wireless or cellular transmitter or transceiver device to transmit an alcohol content or other substance content signal to a wireless or cellular signal receiver and/or monitoring station to help ensure abstinence of the user from the use of alcohol or another substance.

Recovering alcoholics may benefit from the supervision of a sober chaperone such as a sober buddy, sober companion or sober coach to assist a recovering alcoholic in maintaining abstinence from alcohol outside of a treatment facility. Such a sober companion commonly chaperones the recovering alcoholic on a constant basis, or may be available on an on-call basis to accompany a recovering alcoholic periodically or as needed during certain activities. Such supervisory care can be quite expensive, which may have the unfortunate consequence of reducing or eliminating the services of such supervisory care.

People struggling with alcohol often conceal their abuse, making it difficult for concerned family members to confirm their suspicions and intervene. Because alcohol leaves the system quickly, it is important to test for alcohol consumption by using a breathalyzer or another similar alcohol testing method. Confirmation of a drinking problem becomes increasingly difficult during periods when testing for alcohol consumption is not easily enforced, such as during travel for business or college, for example. It would be useful to provide a method for parents to be able to monitor alcohol use anywhere by their children, and for spouses to monitor alcohol use anywhere by their spouses, in order to eliminate suspicions and confirm whether the family member has a drinking problem. It would also be useful to provide a method for companies to deter alcohol abuse by employees during work hours. Industries that rely heavily on driving and have limited employee supervision could also benefit from a method allowing the monitoring of alcohol use by employees as a way to confirm employee sobriety during work hours. Although drug testing is common in the workplace, since alcohol is metabolized relatively quickly, and is not easily tested, it would also be useful to provide a method for immediate confirmation of an employee's alcohol level at any given time.

Court ordered sobriety is also commonly required as a condition of probation or other court imposed rehabilitative or behavior altering programs. Reporting to a stationary facility, one's probation officer, or even one's home in order to be tested for substance use is often an embarrassing and time consuming ordeal that does not facilitate healthy reintegration into society. Thus, the discrete remote monitoring of a person under such a program by the court, or other authority, without requiring the monitored person to excuse themselves from society for more than a brief period of time would be useful in reintegrating the monitored person into society without the awkward and embarrassing effects of traditional monitoring procedures. Such a system is also useful to provide a system of monitoring where those monitored are emboldened to no longer feel like societal outcasts and are thus increasingly motivated to maintain their sobriety.

Currently available remote sobriety monitors involve an intrusive and awkward looking bracelet that requires constant contact with a user's skin. For example U.S. Pat. No. 7,641,611, to Hawthore, et. al., describes an example of one such a remote sobriety monitor requiring the use of skin contacting bracelet. While such monitors enable remote monitoring of blood alcohol levels, users are often stigmatized by their indiscrete presence and therefore find healthy societal interaction while wearing such bracelets difficult.

Non-skin-contact sobriety monitors are available, but they are generally bulky, expensive, inconvenient systems that require a user to periodically return to the sobriety monitor site. For example, the ElmoTech MEMS 3000 system provides a breathalyzer-type sobriety monitor with user image confirmation and remote transmission capabilities. However, the ElmoTech MEMS 3000 sobriety monitor is incapable of being easily transported with the user. Since the user must periodically return to the sobriety monitor site, the user's mobility is extremely limited.

Hand-held breathalyzer-type sobriety monitors such as the monitors in U.S. Pat. No. 6,726,636, to Der Ghazarian et al., are preferable, however because of physical size limitations such hand-held systems do not contain the ability to capture and quickly transmit the user's image for positive identification. Furthermore such hand-held monitors do not transmit complex blood alcohol levels, and instead transmit only simple "pass" or "fail" signals. Thus, recipients of the signals are generally unaware of the user's actual test results. Also, these systems generally are not enabled to provide a vehicle interlock function whereby the breathalyzer is enabled to selectively prohibit vehicle ignition.

There are existing vehicle interlock devices, whereby a breathalyzer is required to enable a vehicle to function; however, such interlock devices are not portable, and further, existing interlock devices can be easily hacked and/or tampered with. For example, a drunk driver can simply have a sober person blow into the breathalyzer to enable vehicle ignition.

It would therefore be desirable to provide a method and system of providing supervisory monitoring of sobriety that is discrete, portable, tamper-proof, and effective, and that can automatically alert a monitoring station of the need for attention and possible corrective or medical action by such a supervisory sober buddy or sober companion on an on-call basis. The present invention meets these and other needs.

BRIEF SUMMARY OF THE INVENTION

Briefly, and in general terms, the present invention provides for a method and system for monitoring sobriety of a user on an automated basis, utilizing a hand-held breath testing device, a wireless or cellular transmitter or transceiver device for wirelessly transmitting results of the breath testing to a wireless or cellular receiver monitoring station. The monitoring station receives the breath testing results (and optionally identification such as a photograph) from the wireless or cellular transmitter or transceiver device, and indicates an alarm or otherwise alerts an on-call monitor when the wireless or cellular transmitter or transceiver is indicated to be off, or when the breath testing results indicate a breath test content greater than a predetermined threshold, or when the received breath is not the breath of the user (which can be determined from the photograph). The method and system can be used in connection with a traditional sober buddy, chaperone service on an on-call basis only, to limit the expense and labor intensiveness of the supervisory care. Such a systems may also be used to monitor abstinence from other drugs which can be taken orally and tested by breath analyzer or the like without the use of a chaperone on a continuing basis.

By using the method and system of the present invention, a family member trying to build back trust in family relationships can prove that they are making behavior changes by sending breath test reports on a predetermined schedule, or when randomly requested by the family. The present invention helps a person prove that they are making healthier choices in life and making steps toward rebuilding trust in family relationships. Families can benefit from knowing that loved ones are sober enough to drive, and the present invention can be used remotely to determine a person's sobriety or that blood alcohol levels are in an acceptable range.

The present invention also provides a method for immediate confirmation of an employee's alcohol level at any given time. Particularly those companies with employees who drive as a part of their employment would benefit by keeping their employees sober during working hours. The present invention also can be used in rehabilitative aftercare, and can be used to monitor multiple patients, and the present invention can be used by a sober companion during times when they were not able to accompany them.

The present invention is also useful for remotely monitoring sobriety in situations in which sobriety has been required as a condition of probation or by courts. In addition, counties and states that sentence an individual to home detention always require sobriety. By incorporating a global positioning satellite ("GPS") tracking module or using the mobile device GPS in the breath testing and identification device, the sobriety and location of individuals placed under home detention can be monitored together, which could eliminate the need for the use of ankle bracelets that are currently in use for home detention.

For families who want to monitor their children or spouses, the sobriety monitoring system of the present invention can send a breath test report and photograph to a monitoring station where the report and photograph can be stored, or can send a breath test report and photograph directly from one mobile device to another, without storage of the report and photograph. A cellular module can alternatively be provided inside the breath testing and identification device that can send a breath test report and photograph directly through Wi-Fi (i.e. wireless network), cell towers, or through other mobile wireless networks such as those that do not rely on fixed infrastructure, for example.

These and other aspects and advantages of the invention will be apparent from the following detailed description and the accompanying drawing, which illustrates by way of example the features of the invention.

BRIEF DESCRIPTION OF THE SEVERAL VIEWS OF THE DRAWING(S)

Illustrated in the accompanying drawing(s) is at least one of the best mode embodiments of the present invention In such drawing(s):

FIG. 4 is a left front perspective of the breath testing and identification device of FIG. 3.

FIG. 5 is a schematic diagram illustrating another embodiment of the method and system for monitoring sobriety, according to the invention.

DETAILED DESCRIPTION OF THE INVENTION

The above described drawing figures illustrate the described apparatus and its method of use in at least one of its preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present apparatus and its method of use.

Described now in detail is a method and system for monitoring sobriety of a user, such as a recovering alcoholic, as an intermediate, automated way of engaging the services of a sober buddy, sober companion, sober coach, or other supervisory care for the user to help ensure against relapse of the user, and to help the user maintain sufficient abstinence from alcohol or another substance to reside and function outside of a treatment facility.

Figure 1:
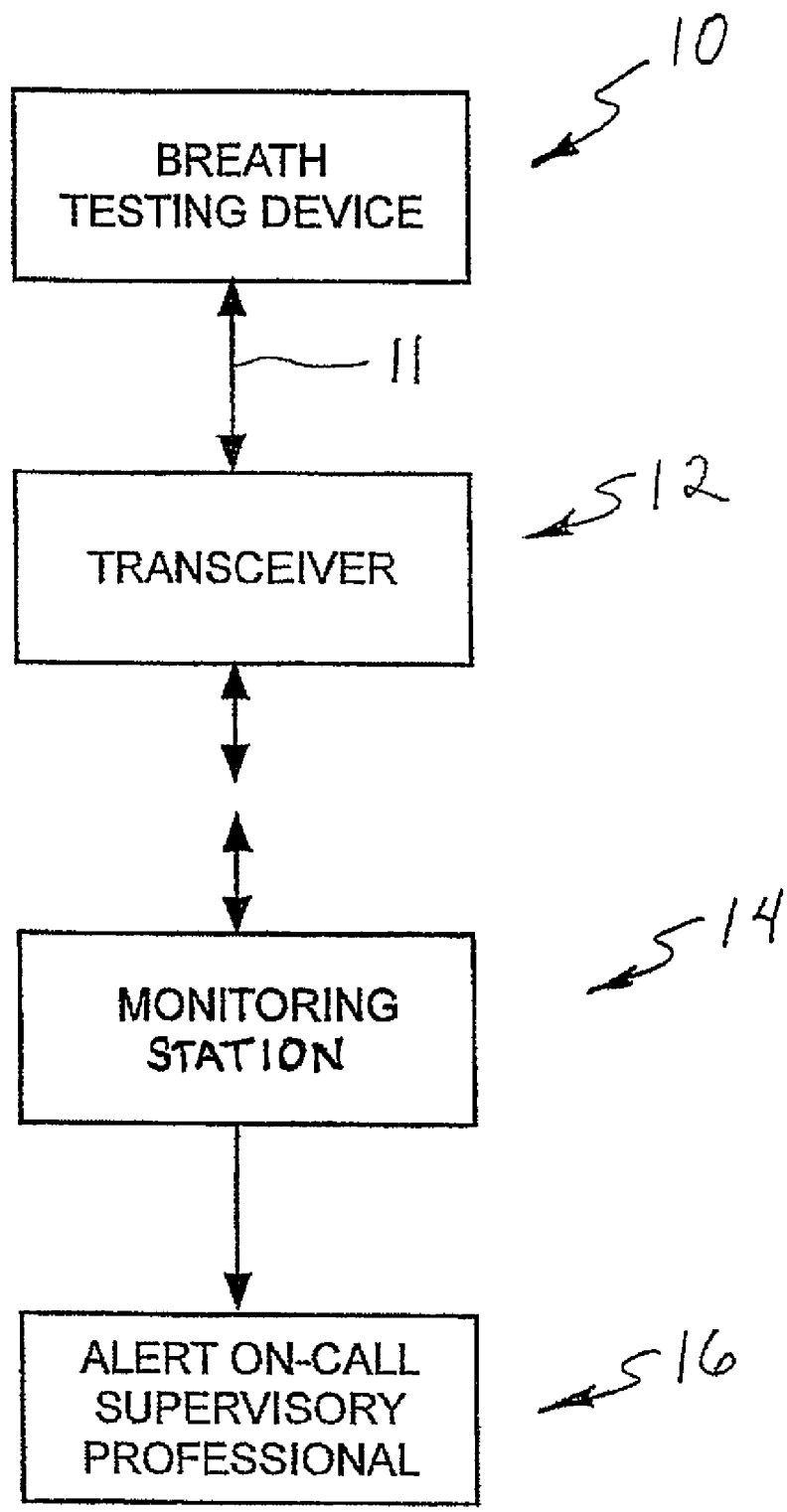
FIG. 1 is a schematic diagram illustrating the method and system for monitoring sobriety, according to the invention.

Referring to FIG. 1, the method and system for monitoring sobriety utilize a hand-held breath testing device 10 for testing alcohol content or content of another substance in the breath of a user, such as a breathalyzer for analyzing the alcohol content of the breath of a user, and for generating an alcohol or other substance content breath test signal 11 indicative of the alcohol or other substance content of the user's breath. In some embodiments, the breath test signal comprises substance content data and user identification data. One presently preferred breath testing device is a breathalyzer type device, such as the iBreath Breathalyzer, usable in combination with an iPod or iPhone, the iPod or iPhone acting as a power source for the iBreath. A wireless or cellular transmitter or transceiver device 12, which can be a cell/smart phone, such as iPhone, for example, can be configured to be connected to the breath testing either directly, such as by an electrical connection, or wirelessly, to receive the breath test signal and identification photo. The wireless or cellular transmitter or transceiver device is also configured to transmit the breath test signal and identification photo periodically over a wireless or cellular network to a wireless or cellular breath test receiving station, which may be any location, device or system where the breath test signal is received, including, for example, a monitoring station 14, a cellular/smart phone, an email account, a website, a network database and a memory device. In one embodiment, the wireless or cellular transmitter or transceiver device 12 is internal to the breath testing device 10 and is a hardware component thereof, the transmitter or transceiver device 12 being configured to transmit the breath test signal directly from the breath testing device via the transmitter or transceiver device 12. The receiving station may be configured to receive the breath test signal, and to indicate an alarm condition or to alert a supervisory monitor 16 if a breath test signal is not received from the wireless or cellular transceiver device periodically, indicating that the wireless or cellular transmitter or transceiver device is off, or if the breath test signal indicates a breath substance content is greater than a predetermined threshold, such as a breath alcohol being greater than a legal limit of blood alcohol content, such as 0.08%, the typical breath alcohol test legal limit, or a lower threshold, as may be desired, or the substance content data, for example a blood alcohol content, for example. In some embodiments, the receiving station may be further configured to receive and convey the breath test signal directly to the supervisory monitor 16 so that the supervisory monitor is directly notified of the substance content data directly.

Figure 2:
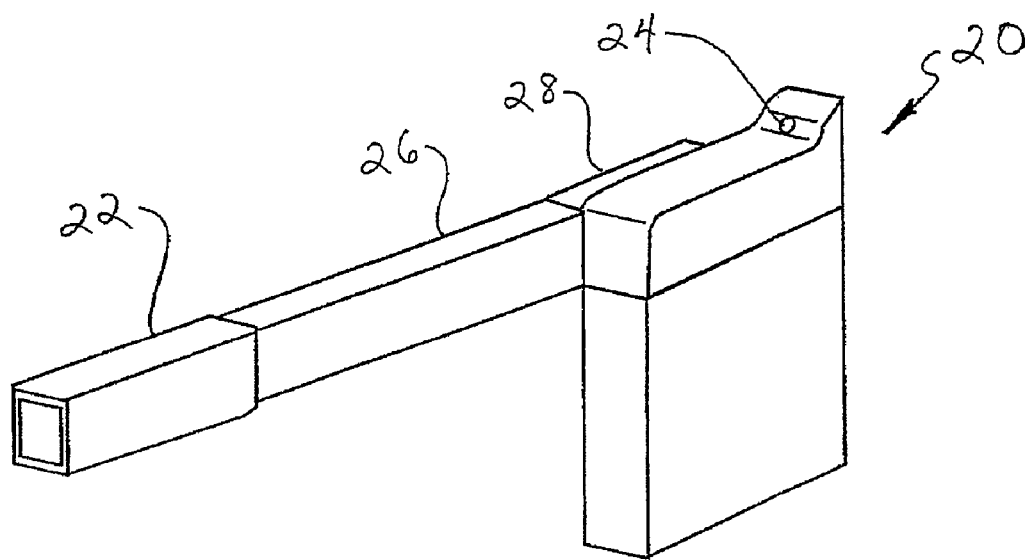
FIG. 2 is a schematic diagram illustrating a breath testing and identification device for use in the method and system of FIG. 1 according to the invention.

Referring to FIG. 2, in one presently preferred embodiment, the present invention provides for a combination breath testing and identification device 20 including a breathalyzer type device, such as a removable breath tester tip 22 configured to be placed at or in a user's mouth during breath testing, and a user identification device 24 comprising, for example a camera. The removable breath tester tip is preferably removably mounted to an end of an extension arm 26 which is in turn connected to a breath analysis and processing portion 28 of the breath testing and identification device. The breath analysis and processing portion 28 comprises a breath testing module 82. A breath test signal module 86 converts the substance content data into the breath test signal. The breath test signal may include, for example, the user's blood alcohol level, or indication that the user's blood alcohol level is below or above a predetermined threshold. The extension arm is preferably a suitable length, such as approximately six to twelve inches, for example, to obtain a still frame photograph or movie suitable for use in accurately identifying the user, although the extension arm may be of an adjustable length to allow setting of an optimum length of the extension arm. The breath testing and identification device may also include a handle (not shown) connected to the camera device or extension arm, for example, for ease of use of the breath testing and identification device. The physical dimensions of the breath testing and identification device are such that it is readily able to be carried by hand, or inserted in to a handbag, purse, pocket or the like. Preferably, the breath testing and identification device is not more than 27 cubic inches in volume, and has, for example, a major axis length of approximately 9 inches, a first minor axis length of approximately 3 inches, and a second minor axis length of approximately 1 inch.

In one embodiment, the user identification device is configured to be directed at the user's face at a suitable distance from the user's face during breath testing, and is configured to take a photograph or movie of the user's face in synchronization with the testing of the user's breath, to provide user identification data for later use in positive identification of the user in association with the breath test signal. As explained below, positive identification of the user in association with the breath test signal may be accomplished by recognition techniques including: facial recognition, voice recognition, DNA recognition, iris recognition, fingerprint recognition, or other recognition techniques now known or developed hereafter.

Figure 8:
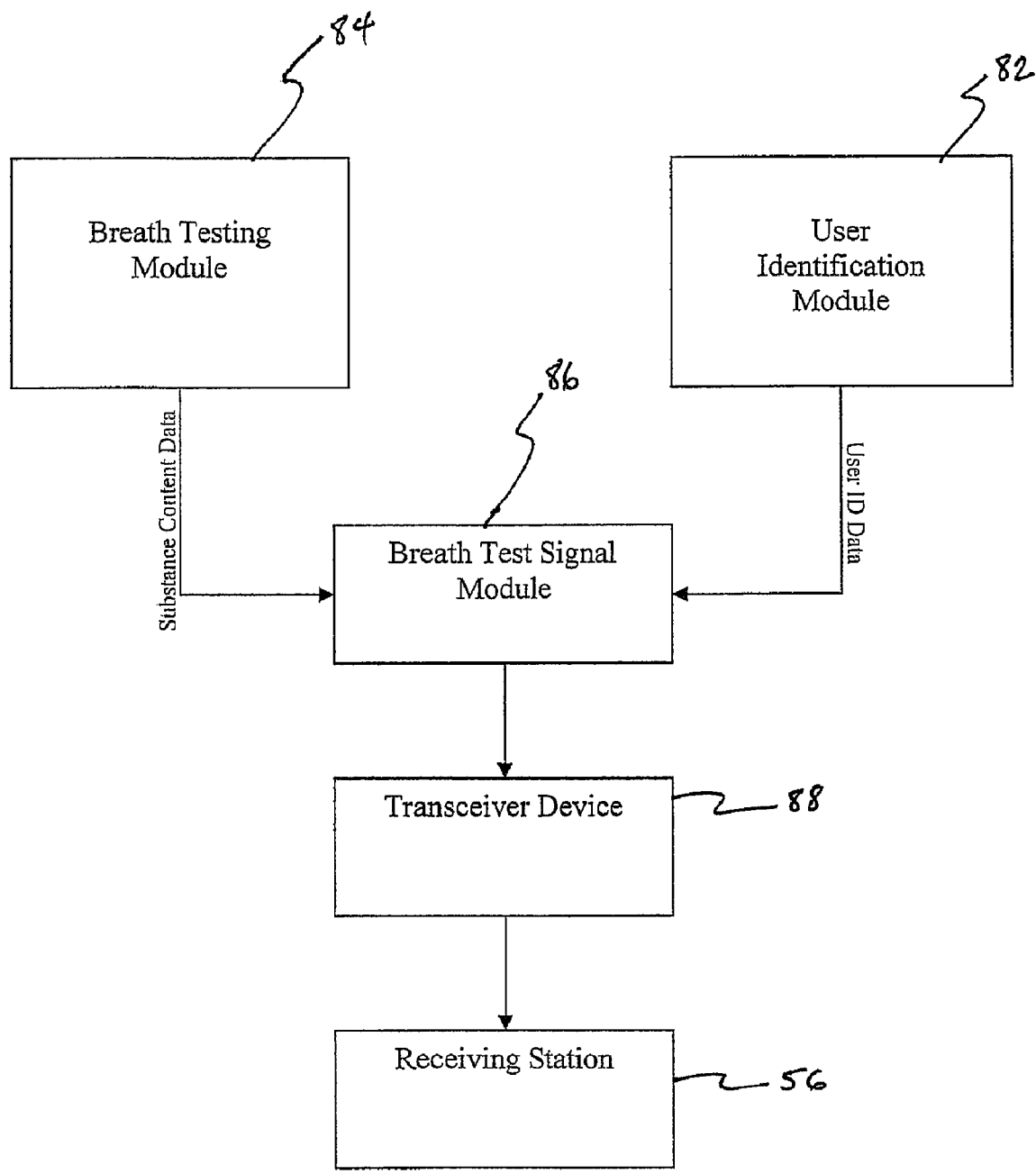
FIG. 8 is a schematic diagram illustrating another the method and system for monitoring sobriety, according to a preferred embodiment of the invention.

Referring to FIG. 8, in one preferred embodiment, the breath testing and identification device comprises a user identification module 82, a breath testing module 84, and a wireless or cellular transceiver 88. The transceiver 88 may be a cell/smart phone, such as iPhone, for example, and can be configured to be connected to the breath testing either directly, such as by an internal or external electrical connection, or wirelessly, to receive the breath test signal. The wireless or cellular transmitter or transceiver device 88 is also configured to transmit the breath test signal periodically over a wireless or cellular network to a wireless or cellular breath test receiving station, for example, a monitoring station 14. During breath testing, the breath testing module 82 converts a user's breath into substance content data. The breath test signal module 86 converts the substance content data into the breath test signal. The breath test signal may include, for example, the user's blood alcohol level, or indication that the user's blood alcohol level is below or above a predetermined threshold. The user identification module 82 is configured to convert a photograph or movie of the user's face into a user identification data, for example, a JPEG image data. The user identification module comprises a compression module (not shown) configured to compresses the user identification data according to a compression process, for example, an implementation variation of standard JPEG compression. The breath test signal module 82 adds the compressed user identification data to the breath test signal and transmits the breath test signal to the breath test receiving station 56, which may be coupled to a website or monitoring station and further may alert an on call supervisory person. Alternatively, the compressed user identification data may be transmitted to the breath test signal receiving station separately from the breath test signal.

Ideally the entire breath test and photography process should take less than 60 seconds, for example, compression of the image data allows a user to offer their breath for testing and have the breath test signal be received by the breath test signal receiving station within 60 seconds.

Figure 3:
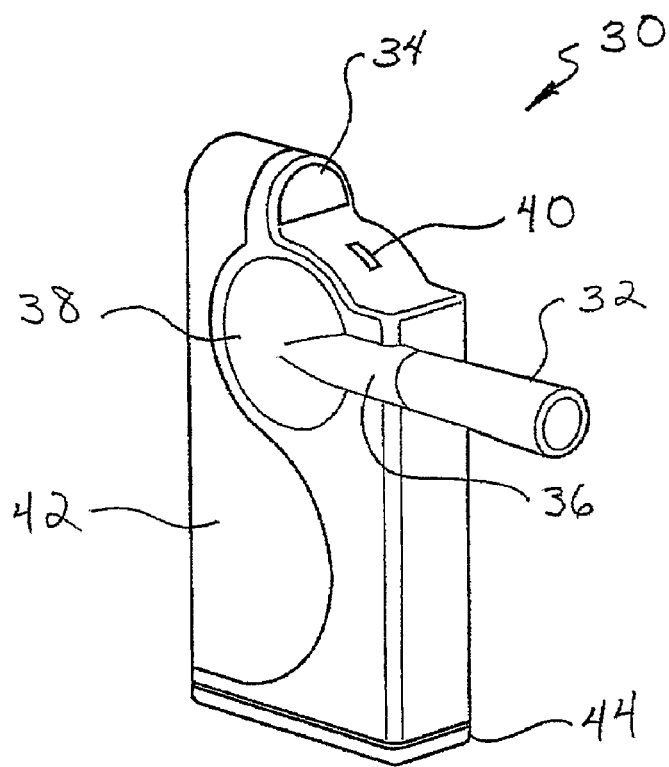
FIG. 3 is a right front perspective illustrating another preferred breath testing and identification device for use in the method and system of FIG. 1 according to the invention.

Referring to FIGS. 3 and 4, in another presently preferred embodiment, the combination breath testing and identification device 30 includes a breathalyzer type device, such as a removable breath tester tip 32 configured to be placed at or in a user's mouth during breath testing, and a camera device 34. The removable breath tester tip is preferably removably mounted to an end of an extension portion 36 which is in turn connected to a breath analysis and processing portion 38 of the breath testing and identification device. The camera device is configured to be directed at the user's face at a suitable distance from the user's face during breath testing, and is configured to take a photograph or movie of the user's face in synchronization with the testing of the user's breath, to provide identification information for later use in positive identification of the user with the test results. The breath testing and identification device may include a status LED 40, such as for indicating when the device is ready for use and when the device has completed breath testing and identification, for example. The breath testing and identification device may also include an over mold grip portion 42, a battery door 44 for installing and maintaining or recharging batteries (not shown) for powering operation of the device, and optionally a cover 46 for breath sensor (not shown) for powering operation of the device. The breath testing and identification device may also include an internal GPS tracking module (not shown) or an internal mobile device GPS (not shown) to provide a GPS location and tracking information signal as well.

Figure 6:
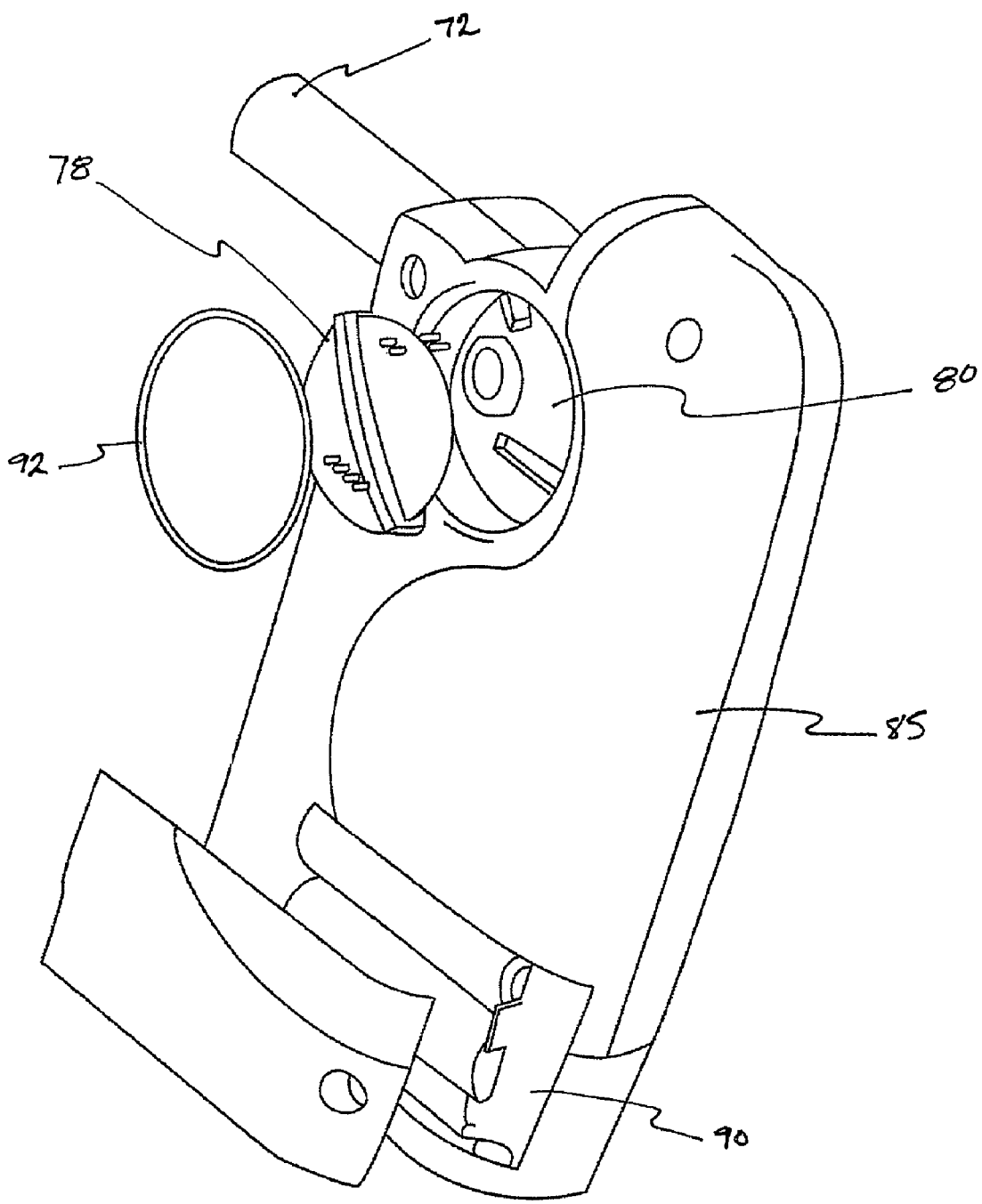
FIG. 6 is an exploded view of the breath testing and identification device according to the invention.
Figure 7:
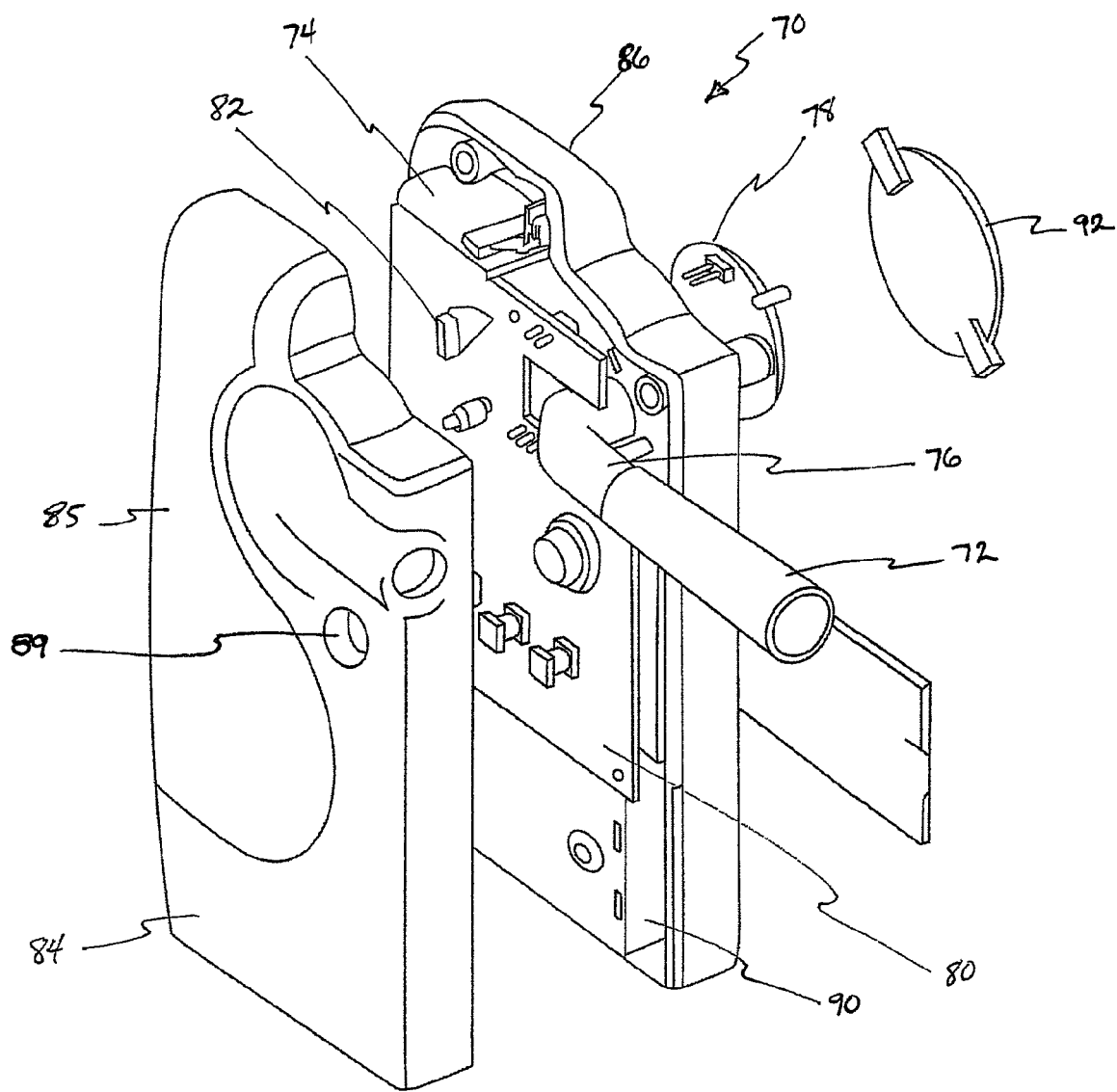
FIG. 7 is an exploded view of the breath testing and identification device according to the invention.

Referring to FIGS. 6 and 7, according to a preferred embodiment, the breath testing and identification device 70 comprises: a breath tube 72; a breath interface tube 76; a camera 74; a breath testing sensor (such as a fuel cell) 78; and a printed circuit board (PCB) assembly 80. The breath tube 72 is configured to be placed at or in a user's mouth during breath testing. In some embodiments, the breath tube removeably fixed to the breath interface tube 76 and is disposable. The breath interface tube 76 is in communication with the breath testing sensor 78, which may be, for example, a semiconductor or a fuel cell breath analyzer. The breath testing sensor 78 is configured to receive the user's breath and calculate substance content data, which may be, for example, a blood alcohol level, and to transmit the substance content data to the PCB assembly 80. The PCB assembly 80 is configured to receive the substance content data and generate a breath test signal therefrom. The PCB assembly 80 is also configured to receive user identification data generated by the camera 74 and to generate the breath test signal from the compressed user identification data and the substance content data. In one embodiment, the PCB is configured to operate a compression process, such as JPEG compression, for example, to compress the user identification data.

A front case 84 and a rear case 86 operate to form a protective housing for the breath testing device 70, and a grip portion 85 provides a textured surface to increase friction and user grip capability. The rear case 86 has a removable sensor cover 92 that is detachable from the rear case 86 to expose the breath testing sensor 78 and permit changing of the breath testing sensor (e.g., in the case of a replaceable fuel cell) 78. A power button 89 is in electrical communication with the PCB assembly 80 and extends beyond the front case 84 so as to be readily accessible to a user. The power button is operable to switch the breath testing device 70 between an on-state and an off-state. A battery compartment 90 operates to house batteries (not shown) that are the electrical power source for the breath testing device. Preferably, the breath testing device will require two AA batteries as an electrical power source. A status indicator light 82, such as an LED, for example is provided in electrical communication with the PCB assembly 80, which indicates a status of the breath testing device. The status indicator light 82 may, for example, indicate that a breath test and/or user identification is occurring, or that a generated breath test signal indicates a substance content greater than a predetermined threshold, or that a generated breath test signal indicates a user identification data does not match with a reference user identification data, or that transmission of the generated breath test signal is occurring, has been successful, or has failed, or that the batteries are running low on power. Corresponding audio signals, such as various types of beeps may be employed as well.

The breath testing and identification device can also be usable in combination with an iPod, iPhone, or other wireless or cellular device such as a BlackBerry, for example, which can serve as a wireless or cellular transmitter or transceiver device, as discussed above, or any other computing device. The wireless or cellular transmitter or transceiver device is preferably configured to be connected to the breath testing and identification device either directly, such as by an electrical connection, or wirelessly, such as via a Bluetooth (i.e. personal area network) connection, for example, to receive a breath test signal and still frame photograph or movie identification information from the breath testing and identification device. The wireless or cellular transmitter or transceiver device is also configured to transmit the breath test signal along with the photograph or movie identification information of the user for each breath test over a wireless or cellular network to a wireless or cellular receiver monitoring station configured to receive the breath test signal, and to indicate an alarm condition or alert the supervisory monitor if a breath test signal is not received from the wireless or cellular transceiver device within a desired timeframe or schedule, indicating that the wireless or cellular transmitter or transceiver device is off, or if the breath test content signal is greater than a predetermined threshold, as discussed above.

The receiving station, for example, a monitoring station, can preferably automatically evaluate the breath test signal and maintain a history of the test time, result and the user identification data for each test. The receiving station can include a database and software for analysis of user identification data, for example, user facial features, for determining whether the user can be identified from each still frame photograph or movie, to confirm or reject the test results, and to determine whether corrective action is required. For example, the receiving station can analyze specific iris or retinal features from one or more eyes of the user for matching with a profile of the user's iris or retinal features, or the receiving station can analyze specific mouth and/or teeth features of the user for matching with a user profile of those features. Iris or retinal identification analysis requires proper alignment and focusing of the camera device, and mouth and/or teeth identification analysis may require an appropriate device for proper placement of the breath testing and identification device and alignment and focusing of the camera device. Multiple internal tooth sensors of a tooth-guard or mouthpiece can be activated by low level electrical signals which can be measured and transmitted by the breath testing and identification device, for use in matching a loading profile of the internal tooth sensors with a user's tooth sensor profile. Additionally, a supervisor may compare the received user identification data with a stored user identification reference in order to positively identify the user.

The monitoring station can either manually or automatically alert a supervisory care professional such as a sober buddy, sober companion or sober coach that is on-call to respond to the alarm condition or alert, in order to take appropriate corrective action. The monitoring station can also preferably provide a variety of reports of the user's testing history or individual test results and still frame photographs or movies used in identification of the user, to allow comprehensive and detailed analysis of the user's testing history, which can be accessed via the Internet as desired.

As is illustrated in FIG. 5, a combination breath testing and identification device 50 may be connected to a mobile wireless or cellular transmitter or transceiver device 52, which can be connected to the breath testing and identification device 50 either directly, such as by an electrical connection, or wirelessly, to receive the breath test signal, photograph or movie identification information, as well as any GPS location and tracking information 54 provided by the breath testing and identification device. The GPS device generates a tracking data that is preferably incorporated into the breath-test signal and transmitted therewith. The wireless or cellular transmitter or transceiver device 52 can in turn transmit the breath test signal, photograph or movie identification information, and tracking data 54 periodically over a wireless or cellular network to a wireless or cellular breath test signal receiving station 56, where the breath test report and photograph or movie identification information can be stored, for example, as in a database at a monitoring station or in a text or e-mail message. Alternatively, the breath alcohol report and photograph or movie identification information, as well as any GPS location and tracking information 54, can be sent directly from one mobile wireless or cellular transmitter or transceiver device to another mobile wireless or cellular transmitter or transceiver device 58, without storage of the breath test report, photograph or movie identification information, and any GPS location and tracking information. The wireless or cellular receiver monitoring station 56 can be configured to receive the breath test signal, photograph or movie identification information and any tracking information 54, and to indicate an alarm condition or alert a supervisory monitor 60 either directly or via a network 62. A cellular module can alternatively be provided inside the breath testing and identification device to send a breath test signal, photograph or movie identification information, and any tracking information 54 directly through Wi-Fi, cell towers, or through a network 62 such as the Internet, or a mobile wireless network, such as those that do not rely on fixed infrastructure, for example. Such data 54 can also be transmitted directly to the supervisory monitor 60.

Figure 9:
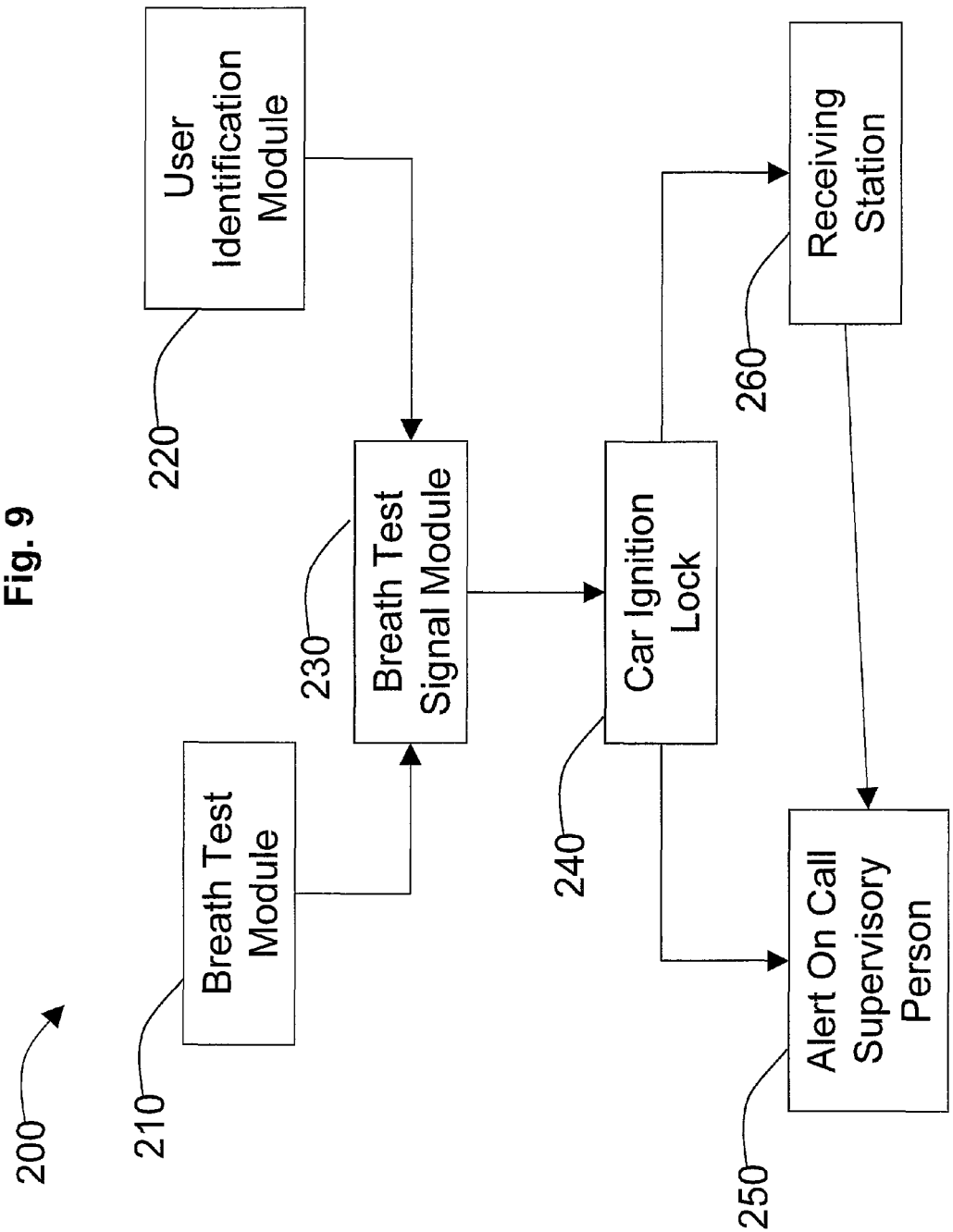
FIG. 9 is a schematic diagram illustrating a vehicle interlock device according to a preferred embodiment of the invention.

Turning to FIG. 9, a mobile breath-testing module 210 and user identification device 220 may also be included in a vehicle ignition interlock signal generating system 200. The output of the breath test module 210 and the user identification module 220 are provided to a breath test signal module 230, which then may provide a signal to enable/disable a car ignition lock 240 based on the data received in accordance with the algorithms described above. The enable/disable signal may be provided to the car ignition lock 240 either wirelessly, e.g., via Bluetooth connection, or a wired connection. In addition, an on-call supervisory person 250 may be alerted, and a receiving station 260, which may be a website and/or monitoring station may also receive the enable/disable signal as well as the actual breath test and user identification data described above.

The embodiments described in detail above are considered novel over the prior art of record and are considered critical to the operation of at least one aspect of the apparatus and its method of use and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements in a claim.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

The scope of this description is to be interpreted only in conjunction with the appended claims and it is made clear, here, that each named inventor believes that the claimed subject matter is what is intended to be patented.

What is claimed is:

1. A portable, cordless, hand-held breath alcohol content testing device, comprising:
    a portable, cordless hand-held case having an inside, an outside, and one or more walls;
    a breath alcohol content sensor housed within the case for sensing a breath alcohol content of a user;
    a breath interface component operatively coupled to the breath alcohol content sensor and exposed within the one or more walls of the case;
    a digital camera housed within the case with a lens exposed within the one or more walls and positioned to capture an image of the user during a breath test;
    a controller housed within the case and electronically coupled to the digital camera and the sensor, the controller configured to cause the camera to capture the image of the user during the breath test and to electronically receive the breath alcohol content and the image of the user; and
    a wireless transceiver housed within the case and electronically coupled to the controller for receiving and wirelessly transmitting the breath alcohol content of the user and electronic image-related data, derived from the image of the user, to a receiving station.

2. The device of claim 1, further comprising an internal battery housed within the case for powering the testing device.

3. The device of claim 1, wherein the wireless transceiver includes circuitry that supports at least one of: a personal area network, a WiFi network, and a cellular network.

4. The device of claim 1, wherein the transceiver wirelessly transmits the breath alcohol content of the user and the image-related data to a server supported website.

5. The device of claim 4, wherein the website is a monitored internet website.

6. The device of claim 1, wherein the transceiver wirelessly transmits the breath alcohol content of the user and the electronic image-related data to a mobile device.

7. The device of claim 1, wherein the transceiver wirelessly transmits the breath alcohol content of the user and the electronic image-related data to a mobile device, and the mobile device transmits the breath alcohol content of the user and the image-related data to a server supported website.

8. The device of claim 7, wherein the website is a monitored internet website.

9. The device of claim 1, further comprising a global positioning unit for identifying a user location during a breath test, wherein the transceiver further wirelessly transmits the user location to the receiving station via at least one of: the personal area network, the WiFi network, and the cellular network.

10. The device of claim 9, wherein the transceiver wirelessly transmits the breath alcohol content of the user, the image-related data, and the user location to a server supported website.

11. The device of claim 10, wherein the website is a monitored internet website.

12. The device of claim 9, wherein the transceiver wirelessly transmits the breath alcohol content of the user, the image-related data, and the user location to a mobile device.

13. The device of claim 9, wherein the transceiver wirelessly transmits the breath alcohol content of the user, the image-related data, and the user location to a mobile device, and the mobile device transmits the breath alcohol content of the user, the image-related data, and the user location to a server supported website.

14. The device of claim 13, wherein the website is a monitored internet website.

15. A system for monitoring sobriety, the system comprising:
- a server coupled to a public network, the server supporting a website configured to display an image of a user in connection with a breath alcohol content of the user; and
- a portable, cordless, hand-held breath alcohol content testing device, comprising:
  - a portable, cordless hand-held case that has one or more walls;
  - a breath alcohol content sensor housed within the case for sensing a breath alcohol content of a user;
  - a breath interface component operatively coupled to the breath alcohol content sensor and exposed to the user within the one or more walls of the case;
  - a digital camera housed within the case with a lens exposed within the one or more walls and positioned above the breath interface component to capture an image of the user during a breath test;
  - a controller housed within the case and electronically coupled to the digital camera and the sensor, the controller configured to cause the camera to capture the image of the user during the breath test and to electronically receive the breath alcohol content and the image of the user; and
  - a wireless transceiver housed within the case and electronically coupled to the controller for receiving and wirelessly transmitting the breath alcohol content of the user and electronic image-related data, derived from the image of the user, to a receiving station.

16. The system of claim 15, wherein the portable, cordless, hand-held breath alcohol content testing device further comprises an internal battery housed within the case for powering the testing device.

17. The system of claim 15, wherein the wireless transceiver includes circuitry that supports at least one of: a personal area network, a WiFi network, and a cellular network.

18. The system of claim 15, further comprising:
- a mobile device having a mobile device transceiver for receiving the breath alcohol content of the user and the image-related data;
- wherein the transceiver further wirelessly transmits the breath alcohol content of the user and the image-related data to the mobile device via at least one of: the personal area network, the WiFi network, and the cellular network.

19. The system of claim 15, further comprising:
- a mobile device having a mobile device transceiver for receiving and wirelessly transmitting the breath alcohol content of the user and the image-related data;
- wherein the transceiver wirelessly transmits the breath alcohol content of the user and the image-related data to the mobile device via at least one of: the personal area network, the WiFi network, and the cellular network; and
- wherein the mobile device transceiver receives and wirelessly transmits the breath alcohol content of the user and the image-related data to the website via at least one of: the personal area network, the WiFi network, and the cellular network.

20. The system of claim 15, further comprising:
- a vehicle interlock device having an interlock transceiver for receiving the breath alcohol content of the user and the image-related data;
- wherein the transceiver further wirelessly transmits the breath alcohol content of the user and the image-related data to the vehicle interlock device via at least one of: the personal area network, the WiFi network, and the cellular network.

21. The system of claim 15,
- wherein the breath testing device further comprises a global positioning unit for identifying a user location during a breath test; and
- wherein the transceiver further wirelessly transmits the user location to the website via at least one of: the personal area network, the WiFi network, and the cellular network.

22. The system of claim 15, wherein the website is a monitored internet website.

* * * * *

(12) INTER PARTES REVIEW CERTIFICATE (86th)
United States Patent
Keays

(10) Number: US 8,381,573 K1
(45) Certificate Issued: Jul. 2, 2015

(54) SOBRIETY MONITORING SYSTEM

(75) Inventor: Brad Keays

(73) Assignee: SOBERLINK, INC.

Trial Number:
IPR2013-00577 filed Sep. 9, 2013

Petitioner: Alcohol Monitoring Systems

Patent Owner: Soberlink, Inc.

Inter Partes Review Certificate for:
Patent No.: 8,381,573
Issued: Feb. 26, 2013
Appl. No.: 12/882,323
Filed: Sep. 15, 2010

The results of IPR2013-00577 are reflected in this inter partes review certificate under 35 U.S.C. 318(b).

INTER PARTES REVIEW CERTIFICATE
U.S. Patent 8,381,573 K1
Trial No. IPR2013-00577
Certificate Issued Jul. 2, 2015

AS A RESULT OF THE INTER PARTES REVIEW PROCEEDING, IT HAS BEEN DETERMINED THAT:

Claims 1-5, 9-11, 15-17, 21 and 22 are cancelled.

\* \* \* \* \*